(12) United States Patent
Wahlstrand et al.

(10) Patent No.: US 9,265,939 B2
(45) Date of Patent: *Feb. 23, 2016

(54) MRI-SAFE IMPLANTABLE MEDICAL DEVICE

(71) Applicant: MEDTRONIC, INC., Minneapolis, MN (US)

(72) Inventors: Carl D. Wahlstrand, Lino Lakes, MN (US); Robert M. Skime, Coon Rapids, MN (US); Gregory A. Hrdlicka, Plymouth, MN (US); James M. Olsen, Plymouth, MN (US); Stephen L. Bolea, Watertown, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/341,355

(22) Filed: Jul. 25, 2014

(65) Prior Publication Data

US 2014/0336738 A1 Nov. 13, 2014

Related U.S. Application Data

(63) Continuation of application No. 14/103,495, filed on Dec. 11, 2013, which is a continuation of application No. 13/803,394, filed on Mar. 14, 2013, now Pat. No. 8,620,454, which is a continuation of application No.

(Continued)

(51) Int. Cl.
*A61N 1/00* (2006.01)
*A61N 1/08* (2006.01)

(Continued)

(52) U.S. Cl.
CPC .. *A61N 1/08* (2013.01); *A61N 1/05* (2013.01); *A61N 1/0534* (2013.01); *A61N 1/0551* (2013.01); *A61N 1/36071* (2013.01); *A61N 2001/086* (2013.01)

(58) Field of Classification Search
CPC ..... A61N 1/05; A61N 1/0534; A61N 1/0551; A61N 1/08; A61N 1/36071; A61N 2001/086
USPC ........................................................ 607/116
See application file for complete search history.

(56) References Cited

U.S. PATENT DOCUMENTS 5,217,010 A 6/1993 Tsitlik et al.
5,727,552 A 3/1998 Ryan (Continued)

FOREIGN PATENT DOCUMENTS

WO 2003/063953 8/2003
WO 2005/003790 1/2005

OTHER PUBLICATIONS

U.S. Appl. No. 14/341,330, Office Action dated Oct. 9, 2014.

(Continued)

*Primary Examiner* — George Manuel
(74) *Attorney, Agent, or Firm* — Withers & Keys, LLC

(57) ABSTRACT

A medical lead is provided for use in a pulse stimulation system of the type which includes a pulse generator for producing electrical stimulation therapy. The lead comprises an elongate insulating body and at least one electrical conductor within the insulating body. The conductor has a proximal end configured to be electrically coupled to the pulse generator and has a DC resistance in the range of 375-2000 ohms. At least one distal electrode is coupled to the conductor.

20 Claims, 7 Drawing Sheets

Related U.S. Application Data

12/954,563, filed on Nov. 24, 2010, now Pat. No. 8,620,453, which is a continuation of application No. 10/945,739, filed on Sep. 20, 2004, now Pat. No. 7,844,343.

(60) Provisional application No. 60/557,991, filed on Mar. 30, 2004.

(51) Int. Cl.
*A61N 1/05* (2006.01)
*A61N 1/36* (2006.01)

(56) References Cited

U.S. PATENT DOCUMENTS

| | | | |
|---|---|---|---|
| 6,032,063 | A | 2/2000 | Hoar et al. |
| 6,844,492 | B1 * | 1/2005 | Wang et al. ............ 174/36 |
| 6,971,391 | B1 | 12/2005 | Wang et al. |
| 7,599,729 | B2 | 10/2009 | Atalar et al. |
| 7,912,552 | B2 | 3/2011 | Przybyszewski |
| 2002/0095084 | A1 | 7/2002 | Vrijheid et al. |
| 2003/0009207 | A1 | 1/2003 | Paspa et al. |
| 2003/0144720 | A1 | 7/2003 | Villaseca et al. |

OTHER PUBLICATIONS

U.S. Appl. No. 14/341,330, Response filed Jan. 9, 2015.
U.S. Appl. No. 14/341,313, Office Action dated Oct. 10, 2014.
U.S. Appl. No. 14/341,313, Response filed Jan. 12, 2015.
U.S. Appl. No. 14/103,495, Office Action dated Jul. 16, 2014.
U.S. Appl. No. 14/103,495, Response filed Dec. 17, 2014.
U.S. Appl. No. 12/954,563, Office Action dated May 14, 2013.
U.S. Appl. No. 12/954,563, Response filed Aug. 14, 2013.
U.S. Appl. No. 13/803,394, Office Action dated May 24, 2013.
U.S. Appl. No. 12/954,563, Response filed Aug. 23, 2013.
Grover, Inductance Calculations: Working Formulas and Tables, "Calculation of Mutual Inductance and Self-Inductance: High Frequency Formulas", Chapter 24, 1946, reprinted 2004, pp. 261-283.
Grandi et al., "Stray Capacitances of Single-Layer Solenoid Air-Core Inductors", IEEE Transactions on Industry Appl. vol. 35, No. 5 Sep./Oct. 1999 pp. 1162-1168.
U.S. Appl. No. 14/341,313, Office Action dated May 26, 2015.
U.S. Appl. No. 14/103,495, Notice of Allowance dated Aug. 24, 2015.
U.S. Appl. No. 14/341,330, Notice of Allowance dated Jun. 15, 2015.

* cited by examiner

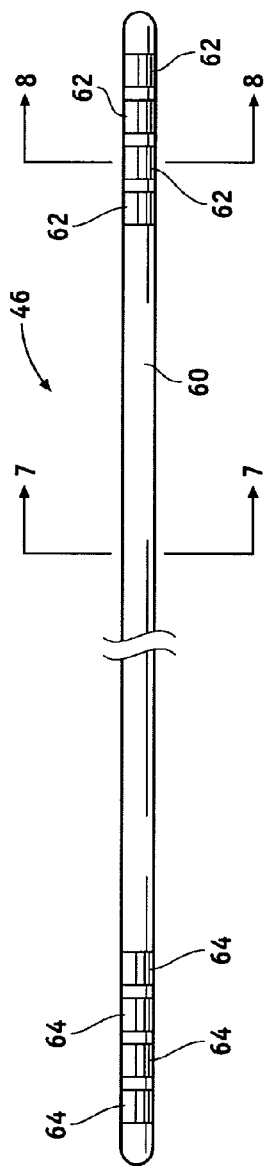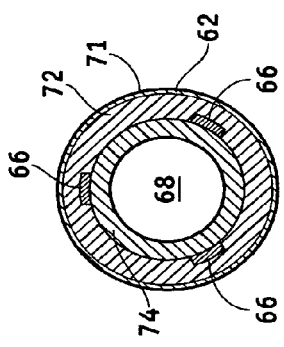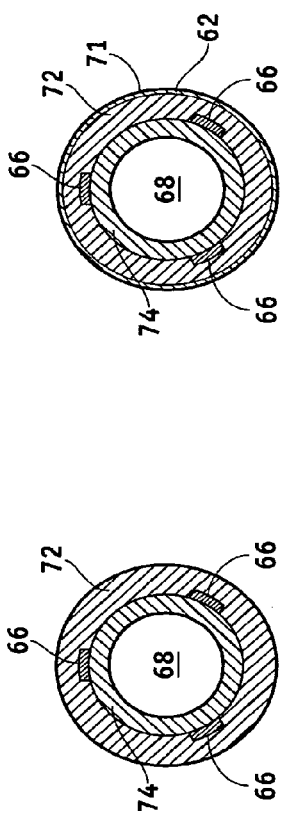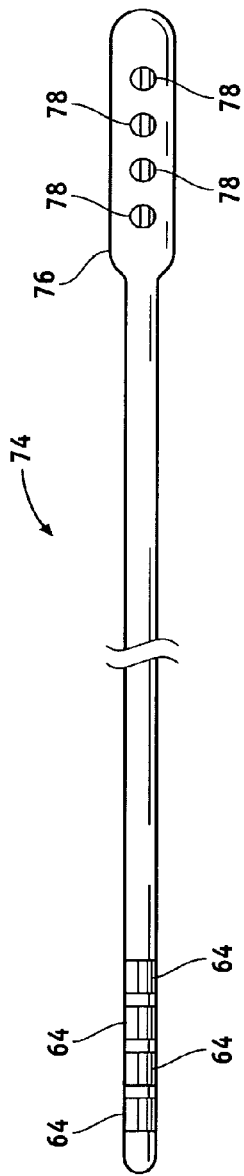

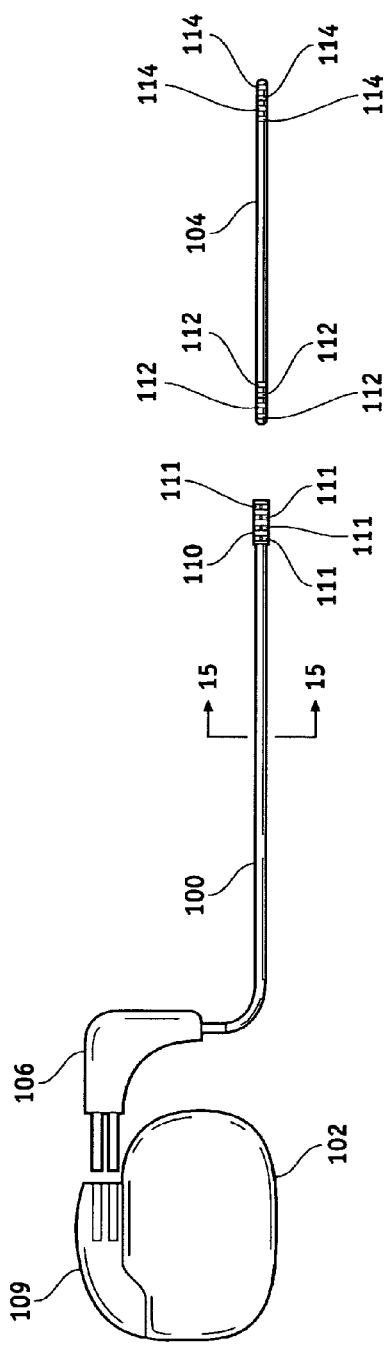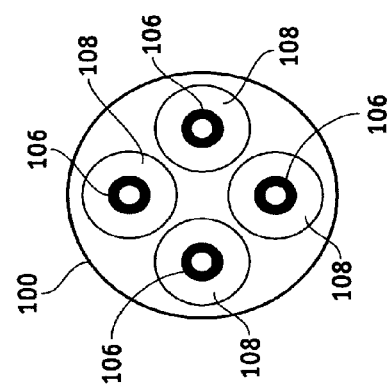
FIG. 14
FIG. 15

MRI-SAFE IMPLANTABLE MEDICAL DEVICE

CROSS-REFERENCES TO RELATED APPLICATIONS

The present application is a continuation of U.S. patent application Ser. No. 12/954,563 filed on Nov. 24, 2010, and entitled MRI-Safe Implantable Medical Device, which is incorporated by reference herein and which is a continuation of U.S. patent application Ser. No. 10/945,739, filed on Sep. 20, 2004, and entitled MRI-Safe Implantable Medical Device, which is incorporated by reference herein and which claims the benefit of U.S. Provisional Application No. 60/557,991 filed Mar. 30, 2004, which is also incorporated by reference herein.

FIELD OF THE INVENTION

The present invention generally relates to implantable medical devices, and more particularly to an implantable medical device such as a neurostimulation system which, when used in an MRI (Magnetic Resonance Imaging) environment does not result in the generation of unwanted heat.

BACKGROUND OF THE INVENTION

Implantable medical devices are commonly used today to treat patients suffering from various ailments. Such implantable devices may be utilized to treat conditions such as pain, incontinence, sleep disorders, and movement disorders such as Parkinson's disease and epilepsy. Such therapies also appear promising in the treatment of a variety of psychological, emotional, and other physiological conditions.

One known type of implantable medical device, a neurostimulator, delivers mild electrical impulses to neural tissue using an electrical lead. For example, to treat pain, electrical impulses may be directed to specific sites. Such neurostimulation may result in effective pain relief and a reduction in the use of pain medications and/or repeat surgeries.

Typically, such devices are totally implantable and may be controlled by a physician or a patient through the use of an external programmer Current systems generally include a non-rechargeable primary cell neurostimulator, a lead extension, and a stimulation lead, and the two main classes of systems may be referred to as: (1) Spinal Cord Stimulation (SCS) and (2) Deep Brain Stimulation (DBS).

An SCS stimulator may be implanted in the abdomen, upper buttock, or pectoral region of a patient and may include at least one extension running from the neurostimulator to the lead or leads which are placed somewhere along the spinal cord. Each of the leads (to be discussed in detail hereinbelow) currently contain from one to eight electrodes. Each extension (likewise to be discussed in detail below) is plugged into or connected to the neurostimulator at a proximal end thereof and is coupled to and interfaces with the lead or leads at a distal end of the extension or extensions.

The implanted neurostimulation system is configured to send mild electrical pulses to the spinal cord. These electrical pulses are delivered through the lead or leads to regions near the spinal cord or the nerve selected for stimulation. Each lead includes a small insulated wire coupled to an electrode at the distal end thereof through which the electrical stimulation is delivered. Typically, the lead also comprises a corresponding number of internal wires to provide separate electrical connection to each electrode such that each electrode may be selectively used to provide stimulation. Connection of the lead to an extension may be accomplished by means of a connector block including, for example, a series or combination of set-screws, ball-seals, etc. The leads are inserted into metal set screw blocks, and metal set screws are manipulated to press the contacts against the blocks to clamp them in place and provide an electrical connection between the lead wires and the blocks. Such an arrangement is shown in U.S. Pat. No. 5,458,629 issued Oct. 17, 1995 and entitled "Implantable Lead Ring Electrode and Method of Making".

A DBS system comprises similar components (i.e. a neurostimulator, at least one extension, and at least one stimulation lead) and may be utilized to provide a variety of different types of electrical stimulation to reduce the occurrence or effects of Parkinson's disease, epileptic seizures, or other undesirable neurological events. In this case, the neurostimulator may be implanted into the pectoral region of the patient. The extension or extensions may extend up through the patient's neck, and the leads/electrodes are implanted in the brain. The leads may interface with the extension just above the ear on both sides of the patient. The distal end of the lead may contain from four to eight electrodes and, as was the case previously, the proximal end of the lead may be connected to the distal end of the extension and held in place by set screws. The proximal portion of the extension plugs into the connector block of the neurostimulator.

Magnetic resonance imaging (MRI) is a relatively new and efficient technique that may be used in the diagnosis of many neurological disorders. It is an anatomical imaging tool which utilizes non-ionizing radiation (i.e. no x-rays or gamma rays) and provides a non-invasive method for the examination of internal structure and function. For example, MRI permits the study of the overall function of the heart in three dimensions significantly better than any other imaging method. Furthermore, imaging with tagging permits the non-invasive study of regional ventricular function.

MRI scanning is widely used in the diagnosis of diseases and injuries to the head. In fact, the MRI is now considered by many to be the preferred standard of care, and failure to prescribe MRI scanning can be considered questionable. For example, approximately sixteen million MRIs were performed in 1996 followed by approximately twenty million in the year 2000. It is projected that forty million MRIs will be performed in 2004.

In an MRI scanner, a magnet creates a strong magnetic field which aligns the protons of hydrogen atoms in the body and then exposes them to radio frequency (RF) energy from a transmitter portion of the scanner. This spins the various protons, and they produce a faint signal that is detected by a receiver portion of the scanner. A computer renders these signals into an image. During this process, three electromagnetic fields are produced; i.e. (1) a static magnetic field, (2) a gradient magnetic field, and (3) a radio frequency (RF) magnetic field. The main or static magnetic field may typically vary between 0.2 and 3.0 Tesla. A nominal value of 1.5 Tesla is approximately equal to 15,000 Gauss which is 30,000 times greater than the Earth's magnetic field of approximately 0.5 Gauss. The time varying or gradient magnetic field may have a maximum strength of approximately 40 milli-Tesla/meter at a frequency of 0-5 KHz. The RF may, for example, produce thousands of watts at frequencies of between 8-128 MHz. For example, up to 20,000 watts may be produced at 64 MHz and a static magnetic field of 1.5 Tesla; that is, 20 times more power than a typical toaster. Thus, questions have arisen regarding the potential risk associated with undesirable interaction between the MRI environment and the above-described neurostimulation systems; e.g. forces and torque on the implantable device within the MRI scanner caused by the static magnetic field, RF-induced heating, induced currents due to gradient magnetic fields, device damage, and image distortion. Of these interactions, the problems associated with induced RF currents in the leads are most deserving of attention since it has been found that the temperature in the leads can rise by as much as 25° Centigrade or higher in an MRI environment.

Accordingly, it would be desirable to provide an implantable medical device that may be safely operated in an MRI environment. It would be further desirable to provide an implantable medical device such as a SCS or DBS neurostimulation system that may be operated in an MRI environment without the generation of significant heat in the leads due to induced RF currents. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

According to an aspect of the invention, there is provided a pulse stimulation system, comprising a pulse generator for producing electrical stimulation and a conductive stimulation lead having a proximal end electrically coupled to the pulse generator, the stimulation lead having a DC resistance in the range of 375-2000 ohms. At least one distal electrode is provided on the distal end. Alternatively, high absolute impedance leads utilizing a combination of DC resistance and impedance due to inductance are provided.

BRIEF DESCRIPTION OF THE DRAWINGS

The present invention will hereinafter be described in conjunction with the accompanying drawing, wherein like reference numerals denote like elements.

FIG. 6 is a top view of the lead shown in FIG. 2;

FIGS. 7 and 8 are cross-sectional views taken along lines 7-7 and 8-8, respectively, in FIG. 6;

FIG. 9 is a top view of an alternate lead configuration;

FIG. 14 is an exploded view of a neurostimulation system;

FIG. 15 is a cross-sectional view of the extension shown in FIG. 14 taken along line 15-15;

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
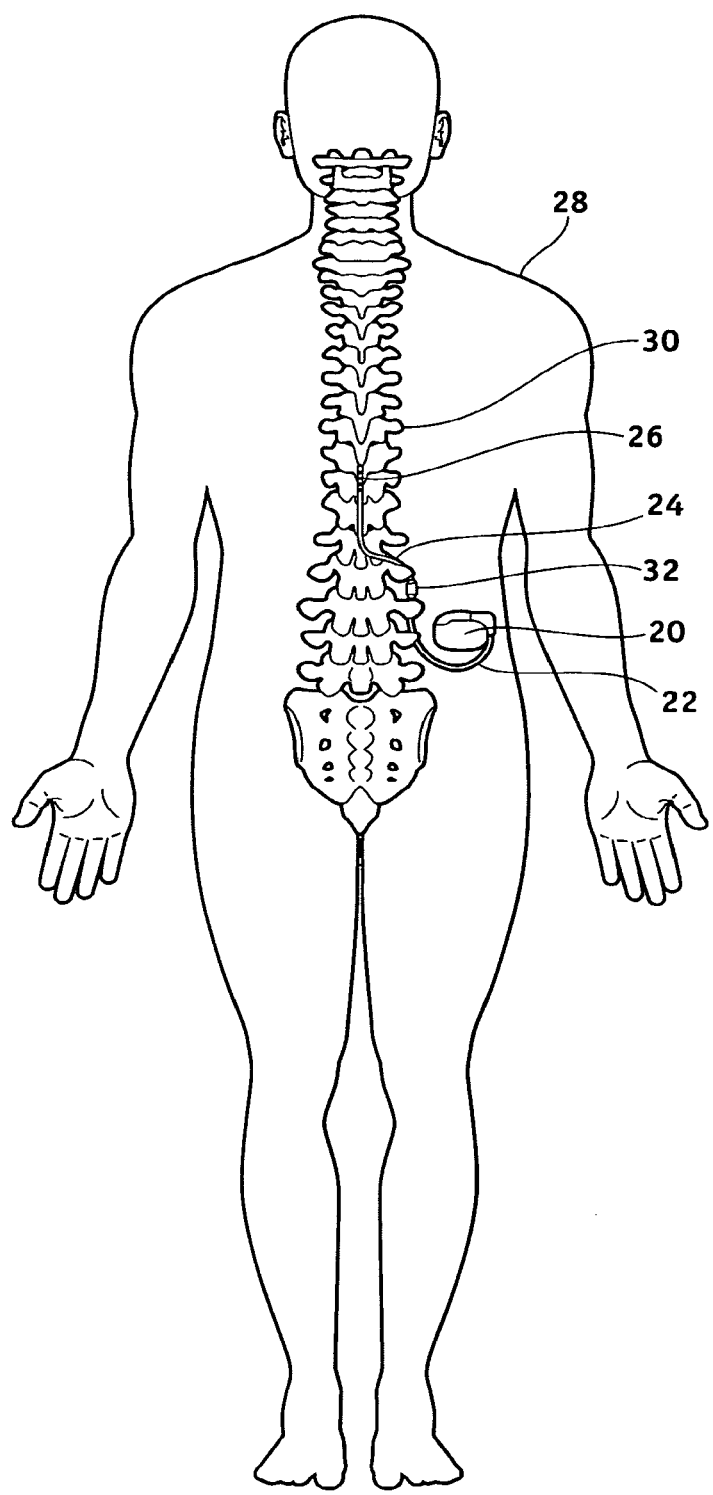
FIG. 1 illustrates a typical spinal cord stimulation system implanted in a patient.

FIG. 1 illustrates a typical SCS system implanted in a patient. As can be seen, the system comprises a pulse generator such as a SCS neurostimulator 20, a lead extension 22 having a proximal end coupled to neurostimulator 20 as will be more fully described below, and a lead 24 having a proximal end coupled to the distal end of extension 22 and having a distal end coupled to one or more electrodes 26. Neurostimulator 20 is typically placed in the abdomen of a patient 28, and lead 24 is placed somewhere along spinal cord 30. As stated previously, neurostimulator 20 may have one or two leads each having four to eight electrodes. Such a system may also include a physician programmer and a patient programmer (not shown). Neurostimulator 20 may be considered to be an implantable pulse generator of the type available from Medtronic, Inc. and capable of generating multiple pulses occurring either simultaneously or one pulse shifting in time with respect to the other, and having independently varying amplitudes and pulse widths. Neurostimulator 20 contains a power source and the electronics for sending precise, electrical pulses to the spinal cord to provide the desired treatment therapy. While neurostimulator 20 typically provides electrical stimulation by way of pulses, other forms of stimulation may be used such as continuous electrical stimulation.

Lead 24 is a small medical wire having special insulation thereon and includes one or more insulated electrical conductors each coupled at their proximal end to a connector and to contacts 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available from Medtronic, Inc.). Lead 24 may contain a paddle at its distant end for housing electrodes 26; e.g. a Medtronic paddle having model number 3587A. Alternatively, electrodes 26 may comprise one or more ring contacts at the distal end of lead 24 as will be more fully described below.

While lead 24 is shown as being implanted in position to stimulate a specific site in spinal cord 30, it could also be positioned along the peripheral nerve or adjacent neural tissue ganglia or may be positioned to stimulate muscle tissue. Furthermore, electrodes/contacts 26 may be epidural, intrathecal or placed into spinal cord 30 itself. Effective spinal cord stimulation may be achieved by any of these lead placements. While the lead connector at proximal end of lead 24 may be coupled directly to neurostimulator 20, the lead connector is typically coupled to lead extension 22 as is shown in FIG. 1. An example of a lead extension is Model 7495 available from Medtronic, Inc.

A physician's programmer (not shown) utilizes telemetry to communicate with the implanted neurostimulator 20 to enable the physician to program and manage a patient's therapy and troubleshoot the system. A typical physician's programmer is available from Medtronic, Inc. and bears Model No. 7432. Similarly, a patient's programmer (also not shown) also uses telemetry to communicate with neurostimulator 20 so as to enable the patient to manage some aspects of their own therapy as defined by the physician. An example of a patient programmer is Model 7434 Itrel® 3 EZ Patient Programmer available from Medtronic, Inc.

Implantation of a neurostimulator typically begins with the implantation of at least one stimulation lead while the patient is under a local anesthetic. While there are many spinal cord lead designs utilized with a number of different implantation techniques, the largest distinction between leads revolves around how they are implanted. For example, surgical leads have been shown to be highly effective, but require a laminectomy for implantation. Percutaneous leads can be introduced through a needle, a much easier procedure. To simplify the following explanation, discussion will focus on percutaneous lead designs, although it will be understood by those skilled in the art that the inventive aspects are equally applicable to surgical leads. After the lead is implanted and positioned, the lead's distal end is typically anchored to minimize movement of the lead after implantation. The lead's proximal end is typically configured to connect to a lead extension 22. The proximal end of the lead extension is then connected to the neurostimulator 20.

Figure 2:
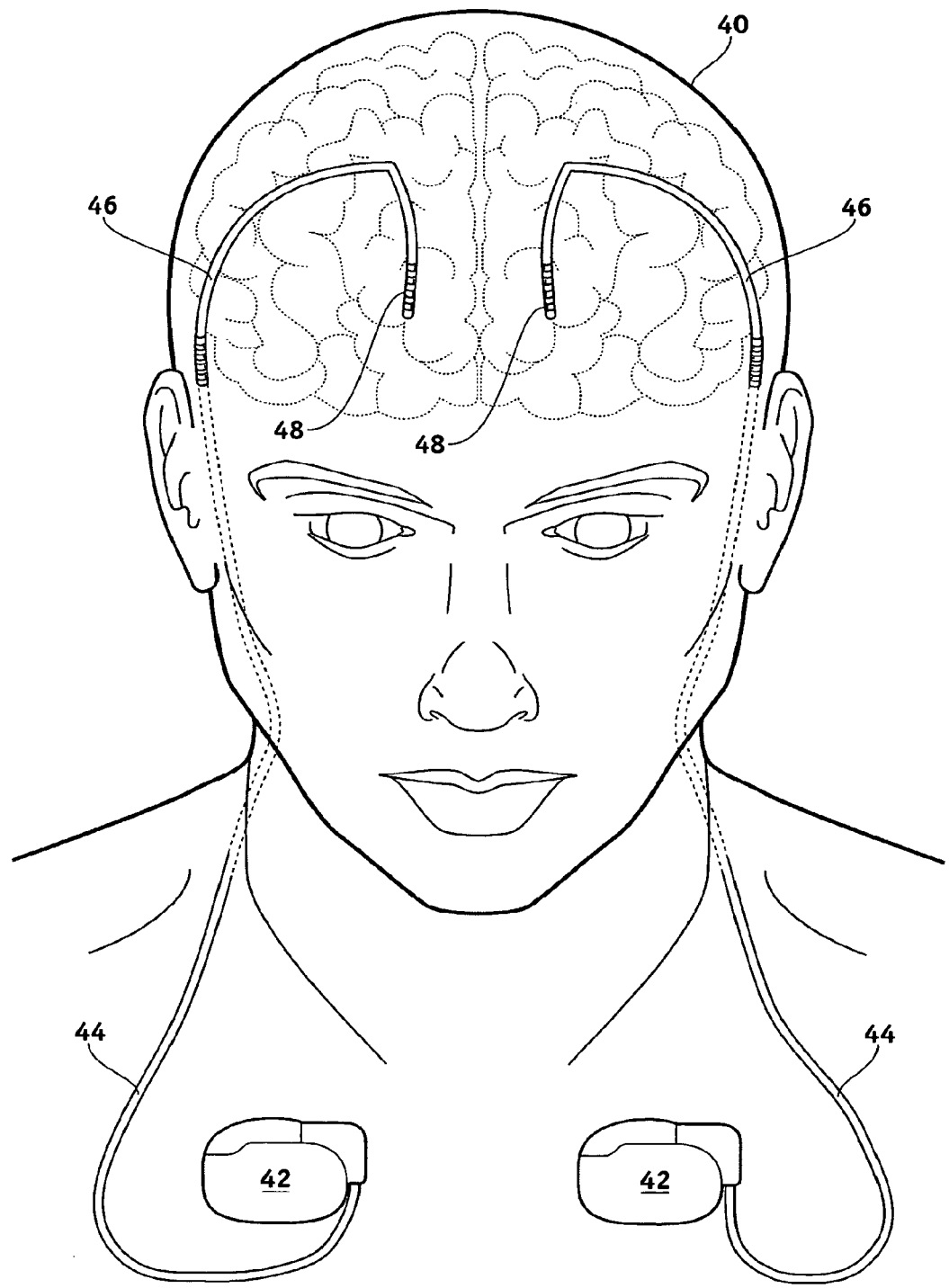
FIG. 2 illustrates a typical deep brain stimulation system implanted in a patient.

FIG. 2 illustrates a DBS system implanted in a patient 40 and comprises substantially the same components as does an SCS; that is, at least one neurostimulator, at least one extension, and at least one stimulation lead containing one or more electrodes. As can be seen, each neurostimulator 42 is implanted in the pectoral region of patient 40. Extensions 44 are deployed up through the patient's neck, and leads 46 are implanted in the patient's brain as is shown at 48. As can be seen, each of leads 46 is connected to its respective extension 44 just above the ear of both sides of patient 40.

Figure 3:
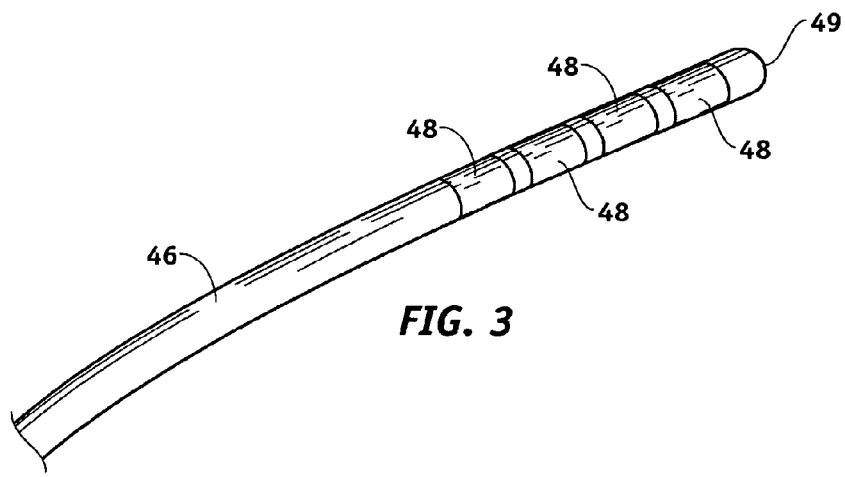
FIG. 3 is an isometric view of the distal end of the lead shown in FIG. 2.

FIG. 3 is an isometric view of the distal end of lead 46. In this case, four ring electrodes 48 are positioned on the distal end of lead 46 and coupled to internal conductors or filers (not shown) contained within lead 46. Again, while four ring electrodes are shown in FIG. 3, it is to be understood that the number of electrodes can vary to suit a particular application.

Figure 5:
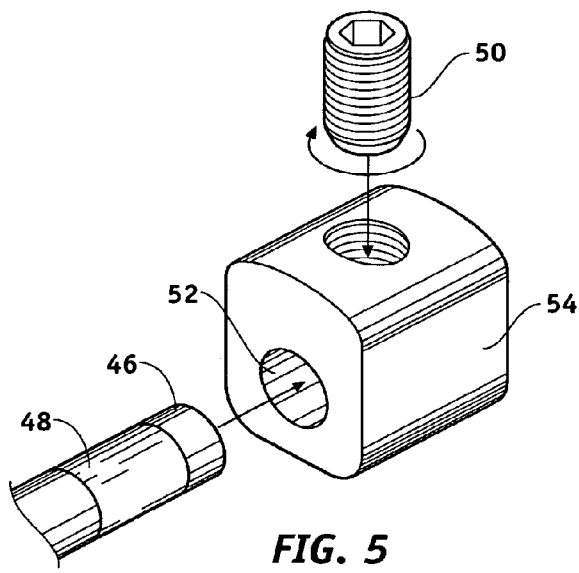
FIG. 5 is an isometric view of an example of a connector screw block suitable for connecting the lead of FIG. 3 to the extension shown in FIG. 4.
Figure 4:
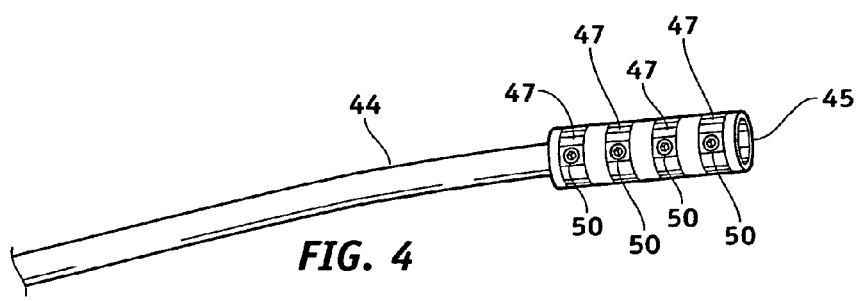
FIG. 4 is an isometric view of the distal end of the extension shown in FIG. 2.

FIG. 4 is an isometric view of the distal end of extension 44, which includes a connector portion 45 having four internal contacts 47. The proximal end of the DBS lead, shown in FIG. 3, plugs into distal connector 45 of extension 44 and is held in place by means of, for example, a plurality (e.g. four) of set screws 50. For example, referring to FIG. 5, lead 46 terminates in a series of proximal electrical ring contacts 48 (only one of which is shown in FIG. 5). Lead 46 may be inserted through an axially aligned series of openings 52 (again only one shown) in screw block 54. With lead 46 so inserted, a series of set screws 50 (only one shown) are screwed into blocks 54 to drive contacts 48 against blocks 54 and secure and electrically couple lead 46. It should be appreciated, however, that other suitable methods for securing lead 46 to extension 44 may be employed. The proximal portion of extension 44 is secured to neurostimulator 42 as is shown in FIGS. 1 and 2.

FIG. 6 is a top view of lead 46 shown in FIG. 2. FIGS. 7 and 8 are cross-sectional views taken along lines 7-7 and 8-8 in FIG. 6. Distal end 60 of lead 46 includes at least one electrode 62 (four are shown). As stated previously, up to eight electrodes may be utilized. Each of electrodes 62 is preferably constructed as is shown in FIG. 8. That is, electrode 62 may comprise a conductive ring 71 on the outer surface of the elongate tubing making up distal shaft 60. Each electrode 62 is electrically coupled to a longitudinal wire 66 (shown in FIGS. 7 and 8) which extends to a contact 64 at the proximal end of lead 46. Longitudinal wires 66 may be of a variety of configurations; e.g. discreet wires, printed circuit conductors, etc. From the arrangement shown in FIG. 6, it should be clear that four conductors or filers run through the body of lead 46 to electrically connect the proximal electrodes 64 to the distal electrodes 66. As will be further discussed below, the longitudinal conductors 66 may be spirally configured along the axis of lead 46 until they reach the connector contacts.

The shaft of lead 46 preferably has a lumen 68 extending therethrough for receiving a stylet that adds a measure of rigidity during installation of the lead. The shaft preferably comprises a comparatively stiffer inner tubing member 70 (e.g. a polyamine, polyamide, high density polyethylene, polypropylene, polycarbonate or the like). Polyamide polymers are preferred. The shaft preferably includes a comparatively softer outer tubing member 72; e.g. silicon or other suitable elastomeric polymer. The conductive rings 71 are preferably of a biocompatible metal such as one selected from the noble group of metals, preferably palladium, platinum or gold and their alloys.

FIG. 9 illustrates an alternative lead 74 wherein distal end 76 is broader or paddle-shaped to support a plurality of distal electrodes 78. A lead of this type is shown in FIG. 1. As was the case with the lead shown in FIGS. 6, 7 and 8, distal electrodes 78 are coupled to contacts 64 each respectively by means of an internal conductor or filer. A more detailed description of the leads shown in the FIGS. 6 and 9 may be found in U.S. Pat. No. 6,529,774 issued Mar. 4, 2003 and entitled "Extradural Leads, Neurostimulator Assemblies, and Processes of Using Them for Somatosensory and Brain Stimulation".

Figure 11:
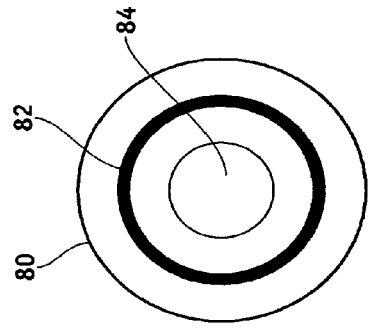
FIGS. 10 and 11 are longitudinal and radial cross-sectional views, respectively, of a helically wound lead of the type shown in FIG. 6.
Figure 10:
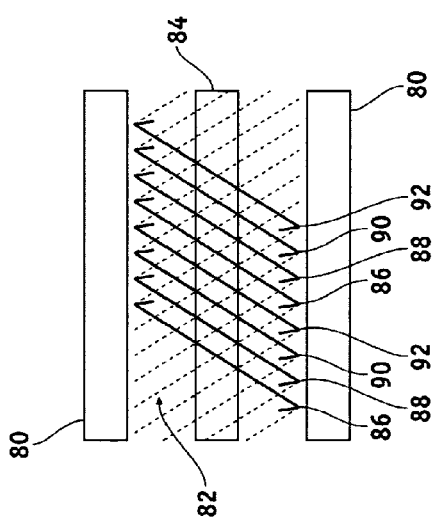

Leads of the type described above may be of the wound helix filer type or of the cabled filer type. FIGS. 10 and 11 are longitudinal and radial cross-sectional views of a helically wound lead of the type shown in FIG. 6. The lead comprises an outer lead body 80; a plurality of helically wound, co-radial lead filers 82; and a stylet lumen 84. As stated previously, a stylet is a stiff, formable insert placed in the lead during implant so as to enable the physician to steer the lead to an appropriate location. FIG. 10 illustrates four separate, co-radially wound filers 86, 88, 90 and 92 which are electrically insulated from each other and electrically couple a single electrode 62 (FIG. 6) to a single contact 64 (FIG. 6).

Figure 13:
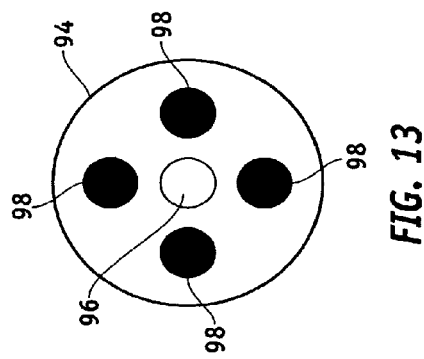
FIGS. 12 and 13 are longitudinal and radial cross-sectional views, respectively, of a cabled lead.
Figure 12:
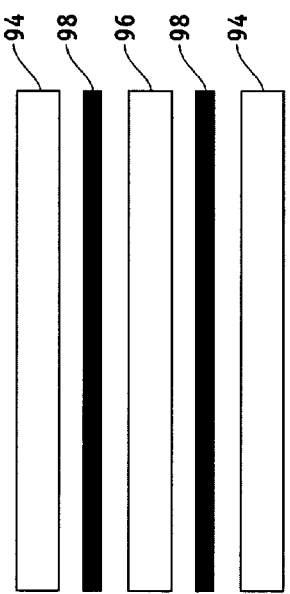

As can be seen, the lead filers 82 have a specific pitch and form a helix of a specific diameter. The helix diameter is relevant in determining the inductance of the lead. These filers themselves also have a specific diameter and are made of a specific material. The filer diameter, material, pitch and helix diameter are relevant in determining the impedance of the lead. In the case of a helically wound lead, the inductance contributes to a frequency dependent impedance. FIGS. 12 and 13 are longitudinal and radially cross-sectional views, respectively, of a cabled lead. The lead comprises outer lead body 94, stylet lumen 96, and a plurality (e.g. four-to-eight) of straight lead filers 98.

FIG. 14 is an exploded view of a neurostimulation system that includes an extension 100 configured to be coupled between a neurostimulator 102 and lead 104. The proximal portion of extension 100 comprises a connector 106 configured to be received or plugged into connector block 109 of neurostimulator 102. The distal end of extension 100 likewise comprises a connector 110 including internal contacts 111 configured to receive the proximal end of lead 104 having contacts 112 thereon. The distal end of lead 104 includes distal electrodes 114.

FIG. 15 is a cross-sectional view of extension 100. Lead extension 100 has a typical diameter of 0.1 inch, which is significantly larger than that of lead 104 so as to make extension 100 more durable than lead 104. Extension 100 differs from lead 104 also in that each filer 106 in lead body 100 is helically wound or coiled in its own lumen 108 and not co-radially wound with the rest of the filers as was the case in lead 104.

The diameter of typical percutaneous leads is approximately 0.05 inch. This diameter is based upon the diameter of the needle utilized in the surgical procedure to deploy the lead and upon other clinical anatomical requirements. The length of such percutaneous SCS leads is based upon other clinical anatomical requirements. The length of such percutaneous SCS leads is typically 28 centimeters; however, other lengths are utilized to meet particular needs of specific patients and to accommodate special implant locations.

Lead length is an important factor in determining the suitability of using the lead in an MRI environment. For example, the greater length of the lead, the larger the effect of loop area that is impacted by the electromagnetic field (i.e. the longer the lead, the larger the antenna). Furthermore, depending on the lead length, there can be standing wave effects that create areas of high current along the lead body. This can be problematic if the areas of high current are near the distal electrodes.

Compared to the helically wound lead, the cable lead has a smaller DC resistance because the length of the straight filer is less than that of a coiled filer and the impedance at frequency is reduced because the inductance has been significantly reduced. It has been determined that the newer cabled filer designs tend to be more problematic in an MRI environment than do the wound helix filer designs. It should be noted that straight filers for cable leads sometimes comprise braided stranded wire that includes a number of smaller strands woven to make up each filer. This being the case, the number of strands could be varied to alter the impedance.

It has been discovered that high lead impedances at MRI operational frequencies can reduce the heating of an electrode during an MRI procedure. The high impedance acts as a choke for current flowing through the lead and, by restricting this current, electrode heating can be reduced. As previously alluded to, leads have been intentionally designed with low impedance to enhance system stimulation efficiency. The simplest way to increase the impedance of a lead is to increase its DC resistance. This may be accomplished in a number of ways that may, if desired, be combined to achieve an optimal impedance.

For example, the resistance R of a lead filer is governed by the equation:

$$R = \frac{L}{\sigma a} \quad \text{Equation (1)}$$

where R is the resistance, L is the length of the filer, a is the conductivity, and a is the cross-sectional area. Decreasing the conductivity and/or the cross-sectional area of the filer will increase resistance proportionally. One typical lead utilizes a stainless steel (non-cored MP35N) filer having a conductivity of $1.1 \times 10^6$ mhos/meter, a diameter of approximately 0.005 inch, and a length of approximately 100 centimeters. Using Equation (1), the resistance R of the lead is approximately seventy-two ohms. If the diameter were reduced to 0.002 inch, R could be increased to approximately 448 ohms (or approximately 126 ohms for a 28 centimeter lead). This is still not sufficient for use in an MRI-safe neurological lead.

Impedance can also be obtained through inductance in accordance with the equation:

$$Z = j(2\pi f)J \quad \text{Equation (2)}$$

where Z is the impedance, L is the inductance, and f is the frequency. Inductance L may be either distributed or discrete. For example, distributed inductance can be created by helically coiling the lead filers in such a way as to achieve the above described optimal impedance at MR frequencies. The inductance is governed by the equation:

$$L = \frac{\mu N^2 A}{l} \quad \text{Equation (3)}$$

where N is the number of turns in the helix, A is the cross-sectional area, l is the length, and μ is the permeability.

Example 1

In the case of a 28 centimeter wound filer lead having a diameter of 0.05 inch and forty turns per inch (i.e. approximately 440 turns for the entire lead), Equation (3) yields an inductance of approximately 1.1 μH. Substituting this value of inductance into Equation (2) yields an absolute impedance of 442 ohms.

Example 2

The DC resistance of a 0.005 inch diameter MP35N straight 28 centimeters filer is approximately 20 ohms. If it is assumed that only inductance can be varied to achieve an impedance in the range of 375 to 2000 ohms at 64 MHz, the inductance, as determined by Equation 2, should be approximately 1.0 μH to 5 μH. At 128 MHz, this range of inductance yields an impedance of approximately 804 to 4000 ohms. For a preferred impedance of 600 ohms, the inductance is approximately 1.5 μH.

Example 3

Optimal impedance at MR frequencies is best obtained through a combination of impedance and inductance. Assume a helically coiled (approximately fifty turns per inch), 28 centimeter long lead having a braided stranded wire having a diameter of 0.002 inch. Equation 3 tells us that the inductance is approximately 1.72 μH. Substitution into Equation 2 yields an impedance of j691 ohms. The DC resistance of such a lead is approximately 1110 ohms. Therefore, Z=1110+j691 ohms Thus, $$|Z| = (1110^2 + 691^2)^{1/2} \text{ or } 1307 \text{ ohms}$$

One known helically wound lead has a DC resistance of approximately 3.3 ohms/centimeter-of-lead. Thus, the DC resistance of 28 centimeter lead is approximately 92.4 ohms, and that of a 100 centimeter lead is approximately 330 ohms. The inductance of this known lead is approximately 31 nH/centimeter-of-lead. Given this information and utilizing Equations (1) and (2), the impedance of known leads is approximately 9.0 ohms/centimeter-of-lead at 43 MHz, 12.9 ohms/centimeter-of-lead at 64 MHz, and 25.1 ohms/centimeter-of-lead at 128 MHz. Thus, a 100 centimeter lead will have an absolute impedance of approximately 900 ohms at 43 MHz, 1290 ohms at 64 MHz, and 2510 ohms at 128 MHz.

In view of the above, the inventive lead should have a DC resistance of at least 375 ohms (preferably approximately 600 ohms) or alternatively at least 5 ohms/centimeter. By utilizing high resistance wires (in the order of $1 \times 10^4$ mhos/centimeter) and assuming a lead length of 100 centimeters, Equation (1) yields a DC resistance of approximately 2000 ohms.

A discrete inductor in the form of, for example, a hybrid component or wound helix in the conductor path of the lead may be utilized to provide inductance, and therefore impedance. In this way, a frequency-dependent impedance can be added at one of more locations in the lead. One such location may be within the lead's distal electrode, which will protect the connections to the inductor. One terminal of the inductor could be attached directly to the electrode, and the other terminal may be attached to the filer. It has been found that placing the inductor close to the distal electrode minimizes heating during an MR scan.

Figure 16:
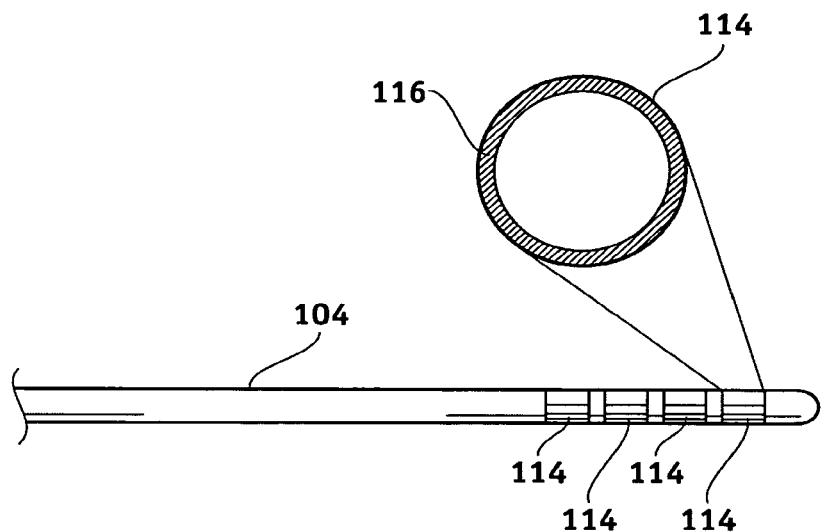
FIG. 16 illustrates a discrete inductor in the distal electrode of a lead.
Figure 17:
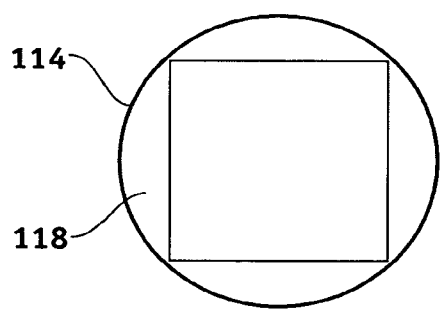
FIG. 17 is a cross-sectional view of a prismatic discrete inductor in a distal electrode.
Figure 18:
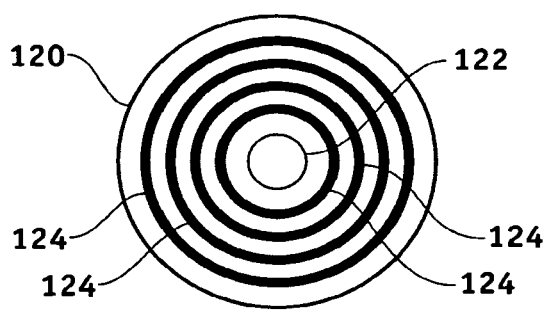
FIG. 18 is a cross-sectional view of a quadripolar coaxially-wound lead.

The discrete inductor comprises a coil of wire of, for example, cylindrical or torroidal construction. While both may be accommodated in a cylindrical package that may fit easily inside a lead electrode, it should be clear that packages of other shapes may be accommodated. For example, FIG. 16 illustrates a cylindrically packaged discrete inductor 116 configured within distal electrode 114. FIG. 17 is a cross-sectional view of a prismatically packaged discrete inductor 118 configured within distal electrode 114, and FIG. 18 is a cross-sectional view of a quadripolar coaxially wound lead including outer lead body 120, stylet lumen 122, and at least four helically and coaxially wound lead filers 124. The lead shown in FIG. 18 provides for a high helix angle and lead inductances that reach or exceed 40 µH/cm. Each filer 124 can be individually insulated or positioned in its own sleeve. Furthermore, each filer 124 may be wound in either direction; and for added strength, certain ones of the filers may be wound in opposite directions.

There are a number of techniques that may be utilized to attach a discrete inductor to a lead electrode; e.g. welding, soldering, using a conductive epoxy, etc. Furthermore, while the discrete inductor is preferably placed inside the distal electrodes, it could also be placed inside the proximal electrodes and still have the benefit of the mechanical protection afforded by the electrode. The discrete inductor could also be placed within the lead body.

While at least one exemplary embodiment has been presented in the foregoing detailed description of the invention, it should be appreciated that a vast number of variations exist. For example, while the invention has been described in connection with neurostimulation systems, the invention is equally applicable to other lead assemblies (e.g. implantable cardiac leads) that may be adversely impacted in high frequency environments such as is encountered during an MRI scan. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

The invention claimed is:

1. A medical system, comprising:
a stimulator for generating electrical stimulation therapy; and
a lead coupled to the stimulator, the lead comprising:
an implantable elongate insulating body;
an electrode on a distal end of the insulating body; and
an electrical conductor within the insulating body that is connected to the electrode, the conductor having an absolute impedance greater than 12.9 ohms per centimeter at 64 MHz.

2. The medical system of claim 1, further comprising a contact on a proximal end of the insulating body, wherein the conductor is connected to the contact.

3. The medical system of claim 1, wherein the conductor includes a discrete inductor.

4. The medical system of claim 3, wherein the discrete inductor is located within the insulating body in proximity to the electrode.

5. The medical system of claim 1, wherein at least a portion of the conductor is helical.

6. The medical system of claim 1, further comprising a second electrical conductor within the insulating body, the electrical conductor being co-radially wound with the second electrical conductor.

7. A medical system comprising:
a stimulator for generating electrical stimulation therapy; and
a lead coupled to the stimulator, the lead comprising:
an implantable elongate insulating body;
an electrode on a distal end of the insulating body;
an electrical conductor within the insulating body that is connected to the electrode, the conductor having an absolute impedance greater than 12.9 ohms per centimeter at 64 MHz, the conductor having discrete elements positioned at multiple locations along the conductor where each of the discrete elements contributes to the absolute impedance.

8. The medical lead of claim 7, further comprising a contact on a proximal end of the insulating body, wherein the conductor is connected to the contact.

9. The medical lead of claim 7, wherein at least a portion of the conductor is helical.

10. The medical lead of claim 7, further comprising a second electrical conductor within the insulating body, the electrical conductor being co-radially wound with the second electrical conductor.

11. A medical system comprising:
a stimulator for generating electrical stimulation therapy; and
a lead coupled to the stimulator, the lead comprising:
an implantable elongate insulating body;
an electrode on a distal end of the insulating body;
an electrical conductor within the insulating body that is connected to the electrode, the conductor having an absolute impedance greater than 12.9 ohms per centimeter at 64 MHz while having a DC resistance less than 12.9 ohms per centimeter.

12. The medical system of claim 11, further comprising a contact on a proximal end of the insulating body, wherein the conductor is connected to the contact.

13. The medical system of claim 11, wherein the conductor includes a discrete inductor.

14. The medical system of claim 13, wherein the discrete inductor is located within the insulating body in proximity to the electrode.

15. The medical system of claim 11, wherein at least a portion of the conductor is helical.

16. The medical system of claim 11, further comprising a second electrical conductor within the insulating body, the electrical conductor being co-radially wound with the second electrical conductor.

17. A medical system comprising:
a stimulator for generating electrical stimulation therapy; and
a lead coupled to the stimulator, the lead comprising:
an implantable elongate insulating body;
a conductive body on a distal end of the insulating body;
an electrical conductor within the insulating body, the conductor having an absolute impedance greater than 12.9 ohms per centimeter at 64 MHz, the conductor having an inductor that is disposed within the conductive body.

18. The medical system of claim 17, wherein the conductor is connected to the conducting body.

19. The medical system of claim 17, wherein at least a portion of the conductor is helical.

20. The medical system of claim 17, further comprising a second electrical conductor within the insulating body, the electrical conductor being co-radially wound with the second electrical conductor.

\* \* \* \* \*